United States Patent
Luce (10) Patent No.: US 9,271,874 B2
(45) Date of Patent: Mar. 1, 2016

(54) SUPPORT FOR AN ABSORBENT ARTICLE

(71) Applicant: Donna E. Luce, Duncanville, TX (US)

(72) Inventor: Donna E. Luce, Duncanville, TX (US)

( * ) Notice: Subject to any disclaimer, the term of this patent is extended or adjusted under 35 U.S.C. 154(b) by 283 days.

(21) Appl. No.: 13/841,731

(22) Filed: Mar. 15, 2013

(65) Prior Publication Data

US 2014/0276526 A1 Sep. 18, 2014

(51) Int. Cl.
*A61F 13/66* (2006.01)
*A61F 13/02* (2006.01)
*A61F 13/82* (2006.01)
*A61F 13/00* (2006.01)

(52) U.S. Cl.
CPC .............. *A61F 13/02* (2013.01); *A61F 13/0203* (2013.01); *A61F 13/82* (2013.01); *A61F 2013/00544* (2013.01); *A61F 2013/00795* (2013.01); *A61F 2013/00978* (2013.01)

(58) Field of Classification Search
CPC ........................................................ A61F 5/448
USPC ......................................................... 604/342
See application file for complete search history.

(56) References Cited

U.S. PATENT DOCUMENTS

| | | |
|---|---|---|
| 1,922,763 A | 8/1933 | Gricks |
| 2,129,054 A | 9/1938 | Geisler |
| 2,496,175 A | 1/1950 | Perry |
| 2,549,649 A | 4/1951 | Van Hove |
| 2,656,838 A | 10/1953 | McConnell |
| 2,675,002 A | 4/1954 | Cesare |
| 2,837,094 A | 6/1958 | Cowles |
| 3,074,404 A | 1/1963 | Robinson |
| 3,398,744 A | 8/1968 | Hooper |
| 4,419,100 A * | 12/1983 | Alexander .............. A61F 5/448 604/339 |
| 4,596,566 A | 6/1986 | Kay |
| 4,636,206 A | 1/1987 | Ederati |
| 4,723,952 A | 2/1988 | Esposito |
| 4,738,257 A | 4/1988 | Meyer |
| 4,865,594 A * | 9/1989 | Thomas ................ A61F 5/4404 604/332 |
| 4,867,749 A | 9/1989 | Steer |
| 5,123,900 A * | 6/1992 | Wick .................... A61F 13/023 602/41 |
| 5,125,917 A | 6/1992 | Whealin |
| 5,178,614 A | 1/1993 | McDowell |
| 5,338,315 A | 8/1994 | Baker |
| 5,429,625 A * | 7/1995 | Holmberg ............... A61F 5/448 604/338 |
| 5,653,701 A | 8/1997 | Millman |
| 5,811,116 A | 9/1998 | Gilman |
| 6,129,715 A | 10/2000 | Cunningham |
| 6,485,476 B1 * | 11/2002 | von Dyck ............... A61F 5/441 600/29 |
| 8,316,985 B2 | 11/2012 | Bain et al. |
| 2007/0135783 A1 | 6/2007 | Scott |
| 2010/0191202 A1 | 7/2010 | Hogard |
| 2010/0241093 A1 | 9/2010 | Hooper |
| 2014/0276526 A1* | 9/2014 | Luce ....................... A61F 13/82 604/393 |

FOREIGN PATENT DOCUMENTS

WO 9716141 5/1997

* cited by examiner

*Primary Examiner* — Tatyana Zalukaeva
*Assistant Examiner* — Guy K Townsend (57) ABSTRACT

A reusable sheath-like support for use with absorbent articles, and specifically used with ostomy appliances. The absorbent article provides an additional level of security and comfort to an ostomate already utilizing a two-piece or one-piece ostomy appliance of the type which is secured to the body with a faceplate. The faceplate provides an adhesive securement means such as a hydrocolloid adhesive member or a combination of hydrocolloid adhesive member and an integral or non-integral adhesive non-woven fabric or adhesive tape.

16 Claims, 5 Drawing Sheets

SUPPORT FOR AN ABSORBENT ARTICLE

CROSS REFERENCE TO RELATED APPLICATIONS

Not applicable.

STATEMENT REGARDING FEDERALLY SPONSORED RESEARCH OR DEVELOPMENT

Not applicable

TECHNICAL FIELD

This invention relates to a support for a disposable absorbent device used with accessories for ostomy pouches.

BACKGROUND OF THE INVENTION

Disposable absorbent devices such as adult incontinence pads, sanitary pads, or pantiliners are provided for the population whose bodily wastes are eliminated thru natural pathways rather than artificial means such as ileostomies, colostomies, or urostomies. An ostomy provides fecal or urinary diversion in emergent and elective settings and is a surgically created opening in which a portion of the intestine is brought through the abdominal wall to form a stoma that may be permanent or temporary depending on the reason for surgery, i.e., disease, injury, birth defects, or cancer. Pouching systems (also called appliances) are used to collect bodily waste through the surgically created openings on the abdomen.

Although appliance styles vary from manufacturer to manufacturer, there are two main types of pouching systems commercially available: one piece systems consisting of a pouch with a built-in skin barrier (also called a faceplate), and two-piece appliances composed of a faceplate and detachable pouch. A flange is provided on the two-piece system in the form of a pair of annular or ring-like rigid plastic parts designed to aid in either securing the pouch to the faceplate or removing the pouch at the user's discretion. A one-piece system connects the faceplate to the pouch by welding or heat sealing. Faceplates are comprised of an adhesive layer formed of a soft, skin-friendly hydrocolloid containing adhesive material and provide therein a centrally located aperture to receive a stoma. Systems may further provide a peel and stick tape on the outer edges of a faceplate for additional adhesion. Sticky skin wipes also help with adhesion of the appliance faceplate and said faceplates are attached to the peristomal region of the user to protect the skin from irritating digestive juices. A pouch may or may not be equipped with a drainable end.

Ostomates are faced with many problems associated with stomas and stoma waste collection pouches. One critical problem faced by ostomates is loss of adhesion of the faceplate from the skin, threatening a resulting loss of containment of waste.

Another problem is that while considerations for stoma placement may be optimum, some part of an appliance faceplate may lie directly underneath the waistband of a wearer's clothing contributing to loss of adhesion.

Fear of public humiliation due to such failures with the faceplate adhesion causes many ostomates to avoid returning to normal lifestyle activities, including work and usual attire. An absorbent article which may or may not be adhesively attached to a support device that is able to provide firm support for a disposable absorbent article for use with ostomy appliances to provide added protection and comfort, would bring peace of mind to an ostomate regarding leakage of primary means.

SUMMARY OF THE INVENTION

A reusable sheath-like support for use with absorbent articles, and specifically used with ostomy appliances. The present invention provides an additional level of security and comfort to an ostomate already utilizing a two-piece or one-piece ostomy appliance of the type which is secured to the body with a faceplate. The faceplate provides an adhesive securement means such as a hydrocolloid adhesive member or a combination of hydrocolloid adhesive member and an integral or non-integral adhesive non-woven fabric or adhesive tape.

DETAILED DESCRIPTION

Figure 1:
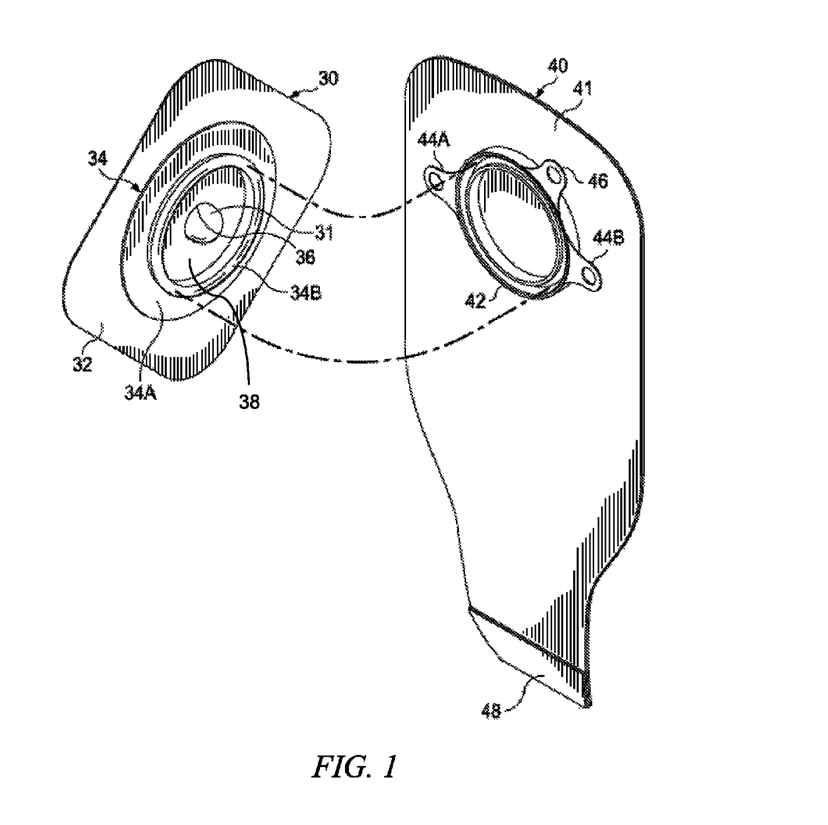
FIG. 1 is a perspective view of an ostomy appliance.

The illustration of FIG. 1 is given to allow for visual understanding of an ostomy appliance system and is not part of the invention of the present application.

FIG. 1 is a typical example of a current, commercially available two-piece ostomy pouching system consisting of a pouch 40, a pouch flange 42, belt tabs 44A and 44B on either side of the pouch flange; a tab on the upper flange facilitates easy removal, and a fold and lock drain 48 for removal of waste. The two-piece appliance also consists of a faceplate 30, with coupling flange 34B, flange base 34A and centrally located aperture 36 to receive a stoma 31. An outer taped portion 32 aids adhesion of an appliance faceplate on the abdomen.

Figure 2:
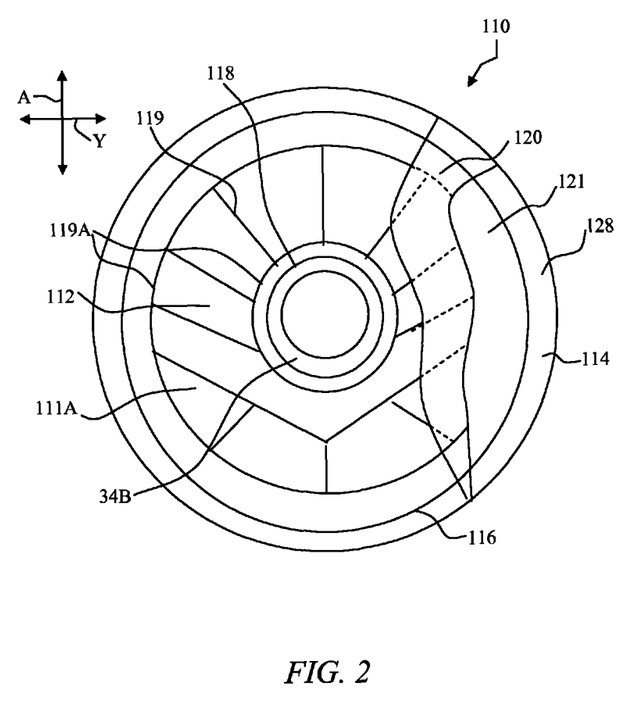
FIG. 2 is one embodiment of an absorbent article for an ostomy appliance

FIG. 2 illustrates one embodiment of an absorbent article 110 disclosed in another application, and for use with an absorbent article support 100 of the present application. The individual components of the absorbent article 110 consists of two sides or two surfaces, a body facing side or body facing surface 111A, and a garment facing side or garment facing surface 111B (not shown), a fluid permeable top sheet 112, a fluid impermeable backsheet 114, and cores 120 and 121 interposed between.

Absorbent core 121 may be a distribution or transfer sheet, its purpose well known in the art, and may be interposed between the topsheet 112 and outer core 120 or alternately, may be a web backing layer interposed between outer core 120 and backsheet 114, but all in accordance with the best mode of manufacture to accomplish the desired functions. Alternately, cores 120 and 121 may be one layer with varied degree of thickness or may be of a consistent thickness throughout. The absorbent article 110 also provides a centrally located aperture 118 through each member component of said absorbent article, for the purpose of maintaining a position upon a faceplate 30 of an ostomy appliance.

The fluid permeable top sheet 112 and fluid impermeable backsheet 114 extend beyond the cores 120, 121 in at least a lateral direction and are joined to one another in the area outside said cores 120, 121 to form an edge seam 116 and/or a garment-facing border 128, and may be joined by gluing, crimping or heat-sealing completely around the periphery of the absorbent article, including sealing the edges of central aperture 118, secured by any means known in the art. Compression lines 119 and compression circles 119A are shown leveraging the use of gravity to help divert and absorb escaping effluent inwardly while compression circles 119A near aperture 118 help prevent leakage at the flange 34B of a faceplate 30.

The outer border 128, having a front, or body facing border 128A, and a back, or garment facing border 128B, (not shown) may be supplied in any shape or form that provides the best protection against leakage if outer border 128 is utilized for taping the absorbent article 110 to the body and said border may be in any shape desirable to provide the best protection for the wearer and is not limited to the illustrations given in the drawings.

FIG. 2 also shows the absorbent article 110 has two centerlines, a transverse (or lateral) centerline A-A and a longitudinal centerline Y-Y. The term "transverse" as used herein, refers to a line, axis, or direction in the plane of the absorbent article 110 that is generally aligned with (e.g., approximately parallel to) the abdomen of a wearer. The terms "longitudinal" used herein, are interchangeable, and refer to a line, axis or direction within the plane of the absorbent article 110 that is generally perpendicular to the transverse direction. In use, the absorbent article 110 is interposed between a faceplate 30 and a pouch 40 and is worn in a transverse direction along line A-A, i.e., generally parallel a user's abdomen. The support 100 likewise having transverse and longitudinal directions, being in the general shape and form of an absorbent article 110 in that the absorbent article 110 is contoured to adhesively attach to the slightly concave body-facing surface 102 of support 100 shown in FIG. 3, not including a garment-facing border 128B.

The absorbent article 110, when worn without a support 100 or not adhesively attached, is applied by guiding the pouch end 48 of an ostomy appliance through central aperture 118 of body facing surface 111A of the topsheet 112, and out garment facing surface 111B, and lifting the article up and over the upper portion of a pouch 41; central aperture 118 is then circumferentially surrounding the coupled appliance flanges 42/34B. The body facing surface 111A is intended to be worn adjacent the faceplate 30 of the wearer's preferred appliance.

In the case of a one-piece appliance, central aperture 118 is placed generally adjacent the connection of the pouch to the faceplate (usually the heat weld) and body facing surface 111A lying on the faceplate 30. In the case the absorbent article is not adhesively attached, the support would be applied in the same fashion as the absorbent article 110 and interposed between the absorbent article 110 and the pouch 40.

Figure 3:
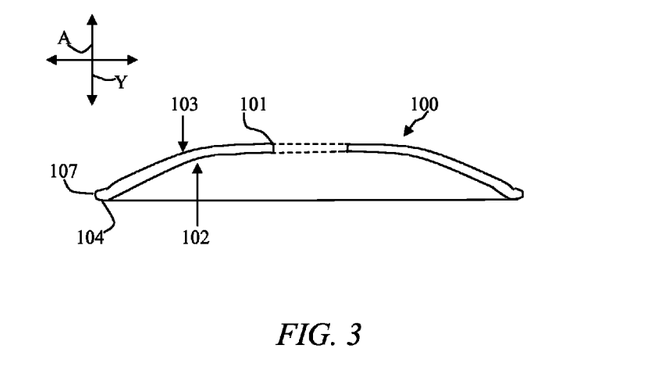
FIG. 3 is a cross-sectional view of an absorbent article support.
Figure 3A:
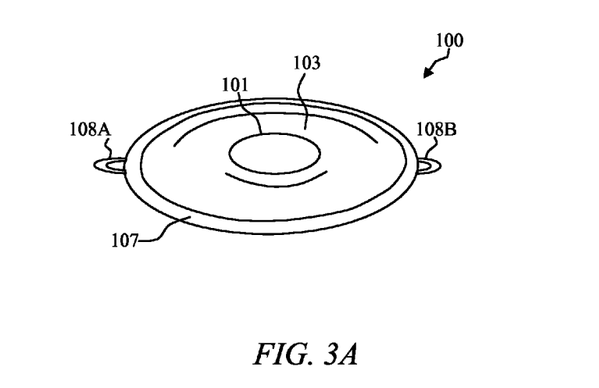
FIG. 3A is a perspective view of an absorbent article support of FIG. 3.

FIG. 3 illustrates a support 100 for an absorbent article and consists of a slightly concave body-facing surface 102, a slightly convex garment facing surface 103, a central aperture 101, a flat body-facing landing zone 104 that may be provided with optional protrusions 105 (not shown), a rolled edge 107 and optional belt tabs 108A & B as shown in FIG. 3B. The support is worn in a transverse direction A-A on the abdomen, (i.e., generally perpendicular to the body).

While an absorbent article 110 worn alone would bring additional comfort and peace of mind to a user, there are additional considerations in favor of a support 100 for an absorbent article 110. One benefit would be to protect the adhesion of a faceplate 30 of an ostomy appliance from the pressure applied from waistbands of form-fitted clothing by means of a more firm material interposed between.

Figure 4:
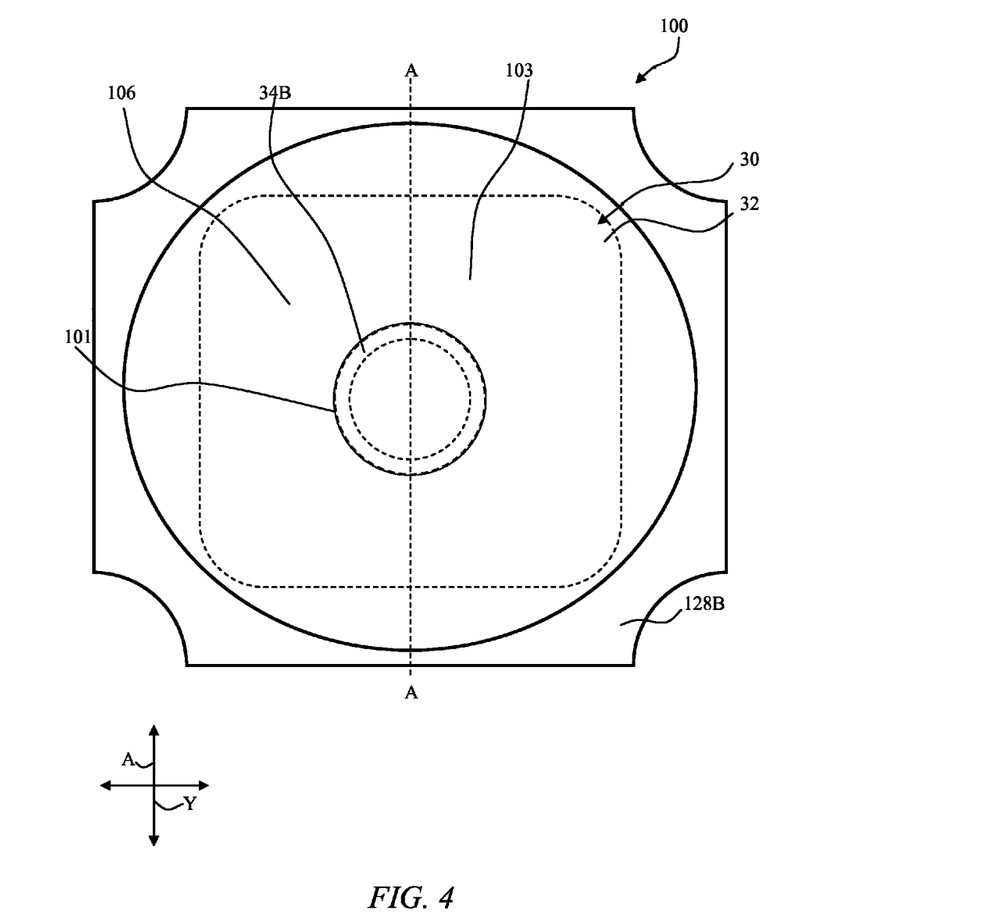
FIG. 4 is a back view of an absorbent article support of FIG. 3 showing its placement on a faceplate with garment facing border of an absorbent article.

A thickness of a support 100 may be at least about 0.06 inches (1/16 in.) more or less, or up to 0.125 inches (1/8 in) more or less, and may be of substantial thickness to provide this protection. Another advantage gained is that a pressure applied to the absorbent article 110 by a flexible, yet rigid material for a support 100 may allow greater absorption in the absorbent article 110 in the event of a leak of the faceplate 30, when worn under form-fitted clothing, allowing a closer engagement of the absorbent article 110 to the area surrounding the flanges 34B/42 of a pouching system and extending outwardly past the periphery of a faceplate 30 (shown in phantom) as can be seen in FIG. 4.

Another beneficial reason is provision of a more sleek profile under form-fitted clothing by keeping an absorbent article close to the body. Still yet another advantageous option is utilizing the outer border 128 of an absorbent article 110 as a means to provide comfort to the skin of the wearer when worn between the support 100 and the skin as illustrated in FIG. 4. Another benefit is to help maintain placement of the absorbent article 110 without adhesive means on said absorbent article 110 or support 100, especially for those who may still be sensitive from surgery or who may have hairy abdomens where an adhesive may be painful to remove. Another benefit is that the absorbent article 110 is held in place by the flange-fit application of a support 100 in order to maintain an advantageous position to capture escaping effluent in case of a leak in the ostomy appliance.

The reusable absorbent article support 100 is applied to the abdomen together with an absorbent article 110 once the absorbent article's backsheet 114 is adhesively attached to the support 100 by strings of adhesive or a pattern of adhesive spots or pressure sensitive adhesives of the kind generally used on pantiliners and the like that are adhered to clothing. The pouch end 48 of an ostomy appliance is guided through central apertures 118/101 of body facing surfaces 111A/102, with the absorbent article 110 adhesively interposed between; the pouch 40 is brought outward of the garment facing surface 103 and the support 100 holding the absorbent article 110 is then lifted up and over the upper portion of a pouch 41.

The absorbent article 110 of body-facing surface 111A now faces an appliance faceplate 30. Central aperture 101 of the support 100 is then circumferentially surrounding the coupled appliance flanges 42/34B or the heat weld of a one-piece ostomy appliance, as the case may be. The adhesively attached absorbent article 110 conjoined with the support 100 is intended to be worn adjacent the faceplate 30 of an ostomy appliance, garment-facing surface 103 of support 100 lying adjacent to a pouch 40.

The central aperture 101 of the support 100 may be provided in varied sizes to accommodate various flange sizes of appliances, and preferably in skin tone colors so as not to be noticed under clothing.

Common flange diameters of appliance faceplates generally range more or less than about 1⅞ inches (47 mm), more or less than about 1¾ inches (44 mm), more or less than about 2¼ inches (57 mm), more or less than about 2¾ (70 mm), and more or less than 4.0 inches (100 mm).

Common and generally square faceplate sizes measured from their peripheral edges may range in diameter approximately more or less than about 1⅞ inch (47 mm) square (infant size), up to more or less than about 4.0 inches (100 mm) square, more or less than about 5.0 inches (127 mm) square, and up to more or less than about 6.0 (152 mm) square, or possibly larger in less common or specially ordered sizes. Circular faceplate diameters or triangular configurations in similar size ranges, as mentioned above, may also be available.

In case an absorbent article 110 does not have an outer border 128, outer periphery 104 on the body-facing surface of support 100 may have optional protrusions 105 that create discontinuous contact facilitating blood flow in the non-contact areas when support 100 lies directly on the skin. Itchiness or tingling, which may be caused by pressure on the skin, may also be relieved by the presence of such support protrusions. Heavy texture, a pattern, or possibly lettering provided in relief the flat body-facing landing zone 104 of the support 100, stamped or molded into the material, may facilitate blood flow in non contact areas when constant pressure is applied from form fitted clothing or a security strap (not shown). Security straps are known in the art of ostomy appliances and may be utilized in this application to hold the conjoined apparatuses close to the body for greater protection against leaks.

As can be seen in FIG. 4, the circular embodiment of an absorbent article support 100 as illustrated, may be appropriate for faceplate shapes that are not circular, or a square shaped absorbent article support 100 may be appropriate for a circular shaped faceplate, etc. and the illustrated embodiment is not meant in any way to limit the scope of the invention, nor is it limited to the particular types or configurations of absorbent articles shown in the drawings. Absorbent article supports 100 may be provided in various colors, sizes of small, medium or large, daytime or nighttime wear. Also, the central aperture 101 may be offset of the longitudinal centerline, allowing added coverage in areas below and beside the appliance faceplate 30 and avoiding a waistband of a wearer whose ostomy appliance is not under a waistband of clothing.

An absorbent article 110 configured to fit a support 100 may have an overall diameter of less than or equal to about 10 inches (254 mm), preferably less than or equal to about 8½ (220 mm), more preferably less than or equal to about 6½ inches (165 mm), and of more than or equal to about 5½ inches (140 mm), and of more than or equal to about 3½ inches (90 mm). The absorbent article (without flaps or circular appendages, if any), may be preferably more than or equal to about 4.0 inches (100 mm), more preferably, more than or equal to 5½ inches (140 mm).

The support 100 may have an overall diameter of more or less than about ¼ inch (0.06 cm) than the absorbent article sizes listed above, extending past the outer periphery of an absorbent article 110 to hold an absorbent article 110 closely to a user's faceplate 30.

The absorbent article support 100 has a slightly domed surface 106 having a central aperture 101 with a flange clearance of at least ⅛ inch (0.125 in.), for ease of use to keep from having to disengage pouch flange 42 from coupling member 34B, and may be formed of any suitable material that may be formed into the desired configurations as explained above and exemplified in the figures. The capacity of the slightly domed surface 106 may vary depending on the absorbent article's thickness, possibly configured for daytime or nighttime use.

Suitable materials for manufacture may be chosen from materials of a non-flexible or flexible grades of plastic, but more preferably flexible, such as polystyrene, polyethylene, polyvinyl chloride, polypropylene or the like, or even thermoplasic polymers such as cyclic olefin copolymers or the like, or more preferably a medical grade thermoplastic elastomers and their blends (TPE) such as made by ExxonMobil Chemical called Santoprene™ which is latex-free in a durometer of about more or less than about 65 durometer, or more or less than about a 75 durometer, preferably more or less than about a 90 durometer, but more preferably, more or less than about 80 durometer. Thermoplastic vulcanizates (TPV) or their blends may also be used having similar durometers.

The absorbent article support 100 may be formed by injection molding, extrusion processes or any other process, i.e., stamped or molded that may impart a degree of rigidity on the garment facing surface 111B of an absorbent article 110 so that when form-fitted clothing is pressed against the layers of an absorbent article 110, pressure to the absorbent article 110 is applied to the abdomen to aid capture of escaping effluent of an ostomy faceplate 30, to absorb and help prevent leakage of intestinal or urinary output in the case of faceplate failure. A flexible material may overlay the edges for example, forming a gasket either removable or adhesively adhered by bonding or overmoulding and co-injection/co-extrusion processes where a more rigid support is formed and edges are softened by use of the more flexible and comfortable edging.

The support 100 may have a means to attach a security strap by tabs 108A and 108B shown in FIG. 3A on either side to hold said support close to the body, or may be attached by hook and loop means applied in a circular, square, random or otherwise, in order to bring the absorbent article close to the body in case form-fitted clothing is not utilized for this purpose.

Figure 5:
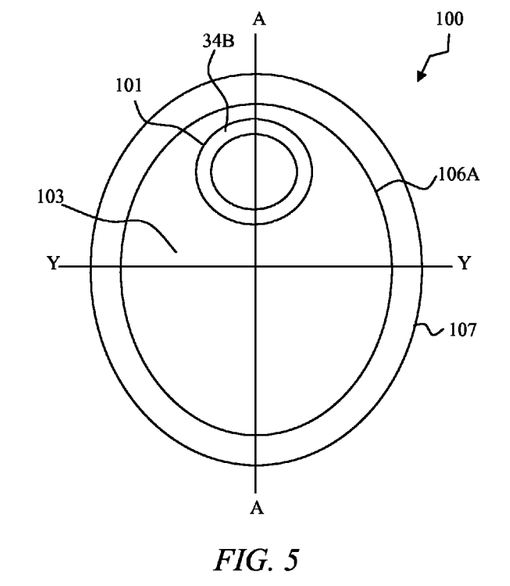
FIG. 5 is a second embodiment of an absorbent article support having an offset aperture.

FIG. 5 alternately illustrates a second embodiment of a plastic absorbent article support 100 illustrated having an offset of center aperture 101 for the purpose of maintaining a position upon the faceplate of an ostomy appliance, and avoiding the waistband of a user who may have an ostomy faceplate 30 that is not under a waistband. The offset may also allow the device to be worn sideways for those who need more protection or comfort to one side or another of their appliance under form-fitted clothing.

The support 100 is made of a very thin material, with an overall thickness of about more or less than about ¹⁄₁₆ inch (0.06 in), but may be provided in any thickness up to more or less than about ⅛ in (0.125 in) and selected from any the above mentioned plastics and having any shape complementary to an absorbent article, having a flattened edge that may or may not rests on the outer border 128 of an absorbent article 110 but may also rest directly on the skin of the user. The absorbent article 110 is attached to the concave or slightly raised body-facing surface 102 of the support 100, as usual, and may be used with an absorbent article 110, which is also off-center in its central aperture 118.

Figure 5A:
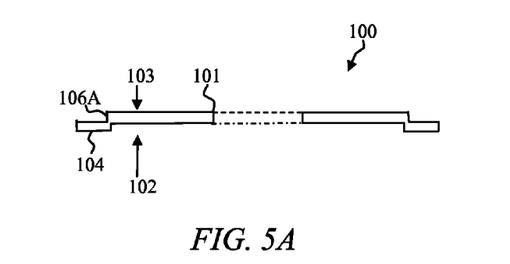
FIG. 5A is a cross-sectional view of the support of FIG. 5.

The absorbent article holder 100 may have a centrally and slightly raised portion 106A on its garment facing surface 103 as seen in FIG. 5A and may be in various shapes such as circular, oblong, triangular or any other shape conforming to or extending beyond a user's faceplate 30 and having a dimension complementary to the absorbent articles disclosed herein; central aperture 101 may be provided to accommodate various pouching system flanges currently available and in any color but preferably the color of skin as not to be seen under clothing.

The absorbent article holder 100 may be formed of various grades of plastic such as those mentioned above, to provide flexibility yet rigid support for an absorbent article while providing a sleek profile for the user worn under form fitted clothing and added protection against leakage, having a rounded or substantially flat distal edge 107 and a substantially flat landing zone 104. The support 100 may have an apertured surface for ventilation and optional protrusions in the form of lettering, texture or a pattern in relief.

While preferred embodiments of the invention have been shown and described, modifications thereof can be made by one skilled in the art without departing from the spirit and teachings of the invention. The embodiments described herein are exemplary only, and are not intended to be limiting.

Many variations and modifications of the invention disclosed herein are possible and are within the scope of the invention.

Having described the invention, I claim:

1. A support for an ostomy appliance absorbent article, comprising:
   a dome-shaped semi-rigid support plate structure having a body-facing concave interior surface and a garment-facing convex exterior surface, said semi-rigid support plate structure adapted to provide support to an ostomy appliance absorbent article that surrounds an ostomy appliance flange that is proximately located near a stoma of an ostomy site;
      said body-facing concave interior surface having a concave shape that creates a concave interior cavity that is adapted to receive said ostomy appliance absorbent article;
      said garment-facing convex exterior surface having a convex shape that lies on the opposite reciprocal side from said body-facing concave interior surface of said support plate structure, wherein said convex shape of said garment-facing convex exterior surface curves outwardly away from said body;
   an aperture extending through said body-facing concave interior surface and garment-facing convex exterior surface of said semi-rigid support plate structure, said aperture adapted to substantially align with said ostomy appliance flange;
   a flat body-facing landing zone edge extending around the circumferential periphery of said body-facing interior concave surface thereby defining an edge boundary of said dome-shaped semi-rigid support plate and encloses the peripheral edge of said body-facing interior concave surface of said semi-rigid support plate structure, said peripheral edge boundary being adjacent the peripheral border of an ostomate faceplate, said flat body-facing landing zone edge configured to lie adjacent to said absorbent article to maintain positioning of absorbent article relative to said ostomate faceplate; and
   wherein said support is made of a flexible, rigid material having a thickness ranging from 1/16 inch to 1/8 inch and is worn in a transverse direction on ostomate abdomen between said ostomate faceplate and an ostomy pouch.

2. The support of claim 1, wherein said aperture is centrally located.

3. The support of claim 1, wherein said aperture is located offset from the center of said support structure.

4. The support of claim 1, wherein said support structure further comprises belt tabs for attachment of a belt.

5. The support of claim 1, wherein said support has a diameter ranging from 3¾ inches to 10¼ inches.

6. A method of making a support for an ostomy appliance absorbent article, comprising the steps of:
   providing dome-shaped semi-rigid support plate structure having a body-facing concave interior surface and a garment-facing convex exterior surface said semi-rigid support plate structure adapted to provide support to an ostomy appliance absorbent article that surrounds an ostomy appliance flange that is proximately located near a stoma of an ostomy site;
      said body-facing concave interior surface having a concave shape that creates a concave interior cavity that is adapted to receive said ostomy appliance absorbent article;
      said garment-facing convex exterior surface having a convex shape that lies on the opposite reciprocal side from said body-facing concave interior surface of said support plate structure, wherein said convex shape of said garment-facing convex exterior support plate surface curves outwardly away from said body;
   providing an aperture extending through said body-facing concave interior surface and garment-facing convex exterior surface of said semi-rigid support plate structure, said aperture adapted to substantially align with said ostomy appliance flange;
   providing a flat body-facing landing zone edge extending around the circumferential periphery of said body-facing interior concave surface of said semi-rigid support plate structure thereby defining an edge boundary of said dome-shaped semi-rigid support plate and encloses the peripheral edge of said body-facing interior concave surface of said semi-rigid support plate structure, said peripheral edge boundary being adjacent the peripheral border of an ostomate faceplate, said flat body-facing landing zone edge configured to lie adjacent to said absorbent article to maintain positioning of said absorbent article relative to said ostomate faceplate and said aperture is configured to essentially surround an ostomy appliance flange; and
   said support being made of a flexible, rigid material and configured to be worn in a transverse direction on ostomate abdomen between said ostomate faceplate and an ostomy pouch.

7. The method of claim 6, wherein said aperture is centrally located.

8. The method of claim 6, wherein said aperture is located offset from the center of said support structure.

9. The method of claim 6, further comprising the step of providing belt tabs on said support for attachment of a belt.

10. The method of claim 6, wherein said support has a thickness ranging from 1/16 inch to 1/8 inch.

11. The support of claim 6, wherein said support has a diameter ranging from 3¾ inches to 10¼ inches.

12. A support for an ostomy appliance absorbent article, comprising:
   a semi-rigid support plate structure having a body-facing surface with a raised interior cavity and a garment-facing raised exterior surface, said semi-rigid support plate structure adapted to provide support to an ostomy appliance absorbent article that surrounds an ostomy appliance flange that is proximately located near a stoma of an ostomy site;
      said raised body-facing surface having a flat shape on its interior that creates an interior cavity raised away from said body, said support plate structure adapted to receive said ostomy appliance absorbent article;
      said garment-facing raised exterior surface having a flat shape that lies on the opposite reciprocal side from said body-facing raised interior cavity surface structure of said support wherein said raised shape of said garment-facing support plate exterior surface is raised outwardly away from said body;
   an aperture extending through said body-facing raised interior cavity surface and garment-facing raised exterior surface of said semi-rigid support plate structure, said aperture adapted to essentially substantially align with said ostomy appliance flange; and a substantially flat landing zone edge extending around the circumferential periphery of said body facing interior cavity surface thereby defining an edge boundary of said dome-shaped semi-rigid support plate and enclosing the peripheral edge of said interior cavity of said body-facing surface of said semi-rigid support plate structure, said peripheral edge boundary being adjacent the peripheral border of an ostomate faceplate, said substantially flat landing zone configured to lie adjacent to said absorbent article to maintain positioning of said absorbent article relative to said ostomate faceplate; and wherein said support is made of a flexible, rigid material having a thickness ranging from 1/16 inch to 1/8 inch and is worn in a transverse direction on ostomate abdomen between said ostomate faceplate and an ostomy pouch.

13. The support of claim 12, wherein said aperture is centrally located.

14. The support of claim 12, wherein said aperture is located offset from the center of said support structure.

15. The support of claim 12, wherein said support structure further comprises belt tabs for attachment of a belt.

16. The support of claim 12, wherein said support has a diameter ranging from 3¾ inches to 10¼ inches.

* * * * *